(12) United States Patent
Jenner

(10) Patent No.: US 6,372,763 B1
(45) Date of Patent: Apr. 16, 2002

(54) TREATMENT AND PREVENTION OF CARDIAC DISORDERS USING SELECTIVE SEROTONIN RE-UPTAKE INHIBITORS (SSRI)

(75) Inventor: Paul Norman Jenner, Amersham (GB)

(73) Assignee: SmithKline Beecham plc, London (GB)

( * ) Notice: Subject to any disclaimer, the term of this patent is extended or adjusted under 35 U.S.C. 154(b) by 0 days.

(21) Appl. No.: 09/462,854

(22) PCT Filed: Jul. 14, 1998

(86) PCT No.: PCT/GB98/02073

§ 371 Date: Mar. 31, 2000

§ 102(e) Date: Mar. 31, 2000

(87) PCT Pub. No.: WO99/03469

PCT Pub. Date: Jan. 28, 1999

(30) Foreign Application Priority Data

Jul. 14, 1997 (GB) ............................................. 9714841

(51) Int. Cl.[7] ................................................ A01N 43/40
(52) U.S. Cl. ...................................................... 514/321
(58) Field of Search ......................................... 514/321

(56) References Cited

FOREIGN PATENT DOCUMENTS

EP 0 768 083 4/1997

OTHER PUBLICATIONS

Carney et al., Clinical Cardiology, 20(3), pp. 196–200 (1997).
Tikal et al., Psychiatricka Lecebna Kosmonosy Ceskoslovenska Psychiatrie, 89(3), pp. 163–165 (1993).
Glassman et al., J. Clin. Psychiatry, 54(2), pp. 16–22 (1993).

*Primary Examiner*—Zohreh Fay
(74) *Attorney, Agent, or Firm*—Wayne J. Dustman

(57) ABSTRACT

A method for treating and/or preventing cardiac disorders in human or non-human animals comprises administering an effective, non-toxic amount of an SSRI or a pharmaceutically acceptable salt thereof, to a human or non-human animal in need thereof.

9 Claims, No Drawings

TREATMENT AND PREVENTION OF CARDIAC DISORDERS USING SELECTIVE SEROTONIN RE-UPTAKE INHIBITORS (SSRI)

The present invention relates to a method for the treatment and/or prevention of cardiac disorders associated with the pathogenesis of thrombosis such as myocardial infarction, using an SSRI such as paroxetine.

Selective serotonin re-uptake inhibitors (SSRI's) are a class of compounds which are well known in the field of treating/preventing depression.

In particularly, U.S. Pat. No. 4 007 196 discloses the compound, (-)-trans-4-(4'-fluorophenyl)-3-(3'4'-methylenedioxy-phenoxymethyl)piperidin, and, in Example 2, a process by which it can be prepared. The compound, which is referred to herein by its common name, paroxetine, is described in the patent as an inhibitor of 5-hydroxytryptamine uptake and, therefore, is of use in the treatment of depression.

Other SSRI include fluoxetine, sertraline, citalopram and fluvoxamine.

It has now been discovered that SSRI's such as paroxetine, fluvoxamine, sertraline and citalopram also have potential therapeutic utility for treating and/or preventing cardiac disorders such as disorders associated with the pathogenesis of thrombosis such as myocardial infarction.

Accordingly, the present invention provides a method for treating and/or preventing cardiac disorders such as disorders associate with the pathogenesis of thrombosis such as myocardial infarction in human or non-human animals, which method comprises administering an effective, non-toxic amount of an SSRI or a pharmaceutically acceptable salt thereof, to human or non-human animals in need thereof.

The present invention also provides the use of and SSRI or a pharmaceutically acceptable salt thereof in the manufacture of a medicament for use in the treatment of and/or prevention of cardiac disorders such as disorders associated with the pathogenesis of thrombosis such as myocardial infarction.

Preferred SSRI's include paroxetine, fluoxetine, citalopram and fluvoxamine.

Examples of pharmaceutically acceptable salts of SSRI's such as fluvoxamine, citalopram sertraline and fluvoxamine are hydrochloride, hydrobromide, acetate and maleate, A preferred salt of paroxetine is the crystalline hydrochloride hemi-hydrate.

An SSRI medicament, for use in the treatment and/or prevention of cardiac disorders such as disorders associated with the pathogenesis of thrombosis such as myocardial infarction may be prepared by admixture of an SSRI or salt thereof with an appropriate carrier, which may contain a diluent, binder, filler, disintegrant, flavouring agent, colouring agent, lubricant or preservative in conventional manner.

Preferably, the medicament is in unit dosage form and in a form adapted for use in the medical or veterinarial fields. For example, such preparations may be in a pack form accompanied by written or printed instructions for use as an agent in the treatment and/or prevention of cardiac disorders such as myocardial infarction.

The suitable dosage range for an SSRI or a salt depends on the severity of the cardiac disorders such as disorders associated with the pathogenesis of thrombosis such as myocardial infarction and on the condition of the patient. It will also depend, inter alia, upon the relation of potency to absorbability and the frequency and route of administration.

An SSRI or a salt thereof may be formulated for administration by any route, and examples are oral, rectal, topical, parenteral, intravenous of intramuscular administration. Preparations may, if desired, be designed to give slow release of the SSRI.

The medicaments may, for example, be in the form of tablets, capsules, sachets, vials, powders, granules, lozenges, reconstitutable powders, or liquid preparations, for example solutions or suspensions, or suppositories.

The medicaments, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycerine; tabletting lubricants, for example magnesium stearate; disintegrants, for example starch, polyvinylpyrrolidone, sodium starch glycollate or microcrystalline cellulose; or pharmaceutically acceptable setting agents such as sodium lauryl sulphate.

Solid medicaments may be obtained by conventional methods of blending, filling, tabletting or the like. Repeated blending operations may be used to distribute paroxetine or a salt thereof throughout those medicaments employing large quantities of fillers. When the medicament is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The medicament may also be in the form of an ingestible capsule, for example of gelatin containing paroxetine or a salt thereof if desired with a carrier or other excipients.

Medicaments for oral administration as liquids may be in the form of, for example, emulsions, syrups, or elixirs, or may be presented as a dry product for reconstitution with water or other suitable vehicle before use. Such liquid medicaments may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin sorbitan monooleate, or acacia; aqueous or non-aqueous vehicles, which include edible oils, for example almond oil, fractionated coconut oil, oily esters, for example water or normal saline; preservatives, for example methyl or propyl p-hydroxybenzoate or sorbic acid; and if desired conventional flavouring or colouring agents.

An SSRI or salt thereof may also be administered by a non-oral route. In accordance with routine pharmaceutical procedure, the medicaments may be formulated, for example for rectal administration as a suppository they may also be formulated for presentation in an injectable form in an aqueous or non-aqueous solution, suspension or emulsion in a pharmaceutically acceptable oil or a mixture of liquids. The liquid may contain bacteriostatic agents, anti-oxidants or other preservatives, buffers or solutes to render the solution isotonic with the blood, thickening agents, suspending agents or other pharmaceutically acceptable additives. Such forms will be presented in unit dose form such as ampoules or disposable injection devices or in multi-does forms such as bottle from which the appropriate dose may be withdrawn or a solid form or concentrate which can be used to prepare an injectable formulation.

As mentioned hereinabove, the effective dose of the SSRI depends on the severity of the cardiac disorders such as disorders associated with the pathogenesis such as myocardial infarction, the condition of the patient an on the frequency and route of administration. A unit dose will generally contain from 2 to 1000 mg and preferably will contain from 30 to 500 mg, in particular 20, 50, 100, 150, 200, 250, 300, 350, 400, 450, or 500 mg. The composition may be administered once or more times daily dose for a 70 kg adult will normally be in the range 100 to 3000 mg. In the case of paroxetine the unit dose will contain from 2 to 20 mg of paroxetine and be administered in multiples, if desired, to give the preceding daily dose.

The present invention further provides a pharmaceutical composition for use in the treatment and/or prevention of cardiac disorders such as disorders associated with the pathogenesis of thrombosis such as myocardial infarction which comprises an effective amount of an SSRI or a pharmaceutically acceptable salt thereof and a pharmaceutically acceptable carrier. Such compositions may be prepared in the manner as hereinbefore described.

The following example demonstrates a suitable pharmaceutical composition:

Example 1

The following were mixed together in a conventional manner and compressed into a tablet in a conventional manner.

22.88 mg Paroxetine hydrochloride hemihydrate 244.12 mg Dibasic calcium phosphate dihydrate 15.00 mg Hydroxypropylmethyl cellulose 2910

15.00 mg Sodium starch glycollate 3.00 mg Magnesium Stearate 300.00 mg Total tablet weight Clinical Data The medical records of 3374 patients who were prescribed on SSRI between February 1989 and January 1993 were examined.

The rate of myocardial infarction for these patients was found to be 0.0204 events per patient year exposure whilst the rate for the general population not taking an SSRI was 0.0226 which demonstrates that patients taking SSRI are statistically less likely to develop a myocardial infarction than those who do not.

What is claimed is:

1. A method for treating and cardiac disorders in human or non-human animals, which method comprises administering an effective, non-toxic amount of a selective serotonin re-uptake inhibiting compound or a pharmaceutically acceptable salt thereof, to a human or non-human animal in need thereof.

2. A method according to claim 1 wherein the selective serotonin re-uptake inhibiting compound is selected from the group consisting of paroxetine, fluoxetine, citalopram and fluvoxamine or a pharmaceutically acceptable salt thereof.

3. A method according to claim 1 wherein the selective serotonin re-uptake inhibiting compound is paroxetine or a pharmaceutically acceptable salt thereof.

4. A method for treating and myocardial infarction in human or non-human animals, which method comprises administering an effective, non-toxic amount of a selective serotonin re-uptake inhibiting compound or a pharmaceutically acceptable salt thereof, to a human or non-human animal in need thereof.

5. A method according to claim 4 wherein the selective serotonin re-uptake inhibiting compound is selected from the group consisting of paroxetine, fluoxetine, citalopram and fluvoxamine or a pharmaceutically acceptable salt thereof.

6. A method according to claim 4 wherein the selective serotonin re-uptake inhibiting compound is paroxetine or a pharmaceutically acceptable salt thereof.

7. A method for treating and the pathogenesis of thrombosis in human or non-human animals, which method comprises administering an effective, non-toxic amount of a selective serotonin re-uptake inhibiting compound or a pharmaceutically acceptable salt thereof, to a human or non-human animal in need thereof.

8. A method according to claim 7 wherein the selective serotonin re-uptake inhibiting compound is selected from the group consisting of paroxetine, fluoxetine, citalopram and fluvoxamine or a pharmaceutically acceptable salt thereof.

9. A method according to claim 7 wherein the selective serotonin re-uptake inhibiting compound is paroxetine or a pharmaceutically acceptable salt thereof.

* * * * *